United States Patent
Clayton

(10) Patent No.: US 12,427,059 B2
(45) Date of Patent: Sep. 30, 2025

(54) ULTRASONIC HANDPIECE ASSEMBLY

(71) Applicant: ZEVEX, INC., Salt Lake City, UT (US)

(72) Inventor: Larry Clayton, Farmington, UT (US)

(73) Assignee: Zevex, Inc., Salt Lake City, UT (US)

( * ) Notice: Subject to any disclaimer, the term of this patent is extended or adjusted under 35 U.S.C. 154(b) by 246 days.

(21) Appl. No.: 18/195,450

(22) Filed: May 10, 2023

(65) Prior Publication Data

US 2024/0374423 A1 Nov. 14, 2024

(51) Int. Cl.
*A61F 9/007* (2006.01)
*B06B 1/06* (2006.01)

(52) U.S. Cl.
CPC ........ *A61F 9/00745* (2013.01); *B06B 1/0614* (2013.01); *B06B 2201/76* (2013.01)

(58) Field of Classification Search
CPC ..... A61F 9/00745; A61B 2017/320098; B06B 1/0614; B06B 2201/76
See application file for complete search history.

(56) References Cited

U.S. PATENT DOCUMENTS

| | | | |
|---|---|---|---|
| 5,112,300 A | 5/1992 | Ureche | |
| 6,402,769 B1 | 6/2002 | Boukhny | |
| 8,395,299 B2 | 3/2013 | Bromfield | |
| 8,610,334 B2 | 12/2013 | Bromfield | |
| 9,498,245 B2 * | 11/2016 | Voegele | A61B 8/4209 |
| 10,137,033 B2 | 11/2018 | Clayton | |
| 2001/0011176 A1 | 8/2001 | Boukhny | |
| 2001/0047166 A1 * | 11/2001 | Wuchinich | A61B 17/320068 606/1 |
| 2003/0125620 A1 * | 7/2003 | Satou | B06B 3/00 600/437 |
| 2007/0232928 A1 * | 10/2007 | Wiener | A61B 8/4455 600/459 |
| 2011/0278988 A1 * | 11/2011 | Young | B06B 3/00 310/328 |
| 2012/0072197 A1 | 3/2012 | Ovchinnikov | |
| 2012/0293044 A1 * | 11/2012 | Bromfield | B06B 1/0611 310/323.18 |

(Continued)

OTHER PUBLICATIONS

Rozenberg, L.D., editor, Sources of High-Intensity Ultrasound, 1969, vol. 2, Chapter 5, pp. 173-183, Plenum Press, New York, U.S.A.

*Primary Examiner* — Andrew Restaino
(74) *Attorney, Agent, or Firm* — Hodgson Russ LLP

(57) ABSTRACT

An ultrasonic handpiece assembly has a horn, a rear mass attached to a rear end of the horn, a needle attached to a front end of the horn, a stack of piezoelectric elements arranged coaxially about the horn, and an L-T spring arranged coaxially about the horn behind the stack. The horn includes a low gain section in front of the stack and a high gain section in front of the low gain section. The assembly has a first L-T mode, a T mode, a second L-T mode, and an L mode at different resonant frequencies. The low gain horn section includes a circumferential groove located at a vibrational node of the L-T mode. Frequency separation between the first L-T mode and T mode results in torsional vibration of the first L-T mode interacting constructively with torsional vibration of the T mode, thereby increasing torsional stroke in the T mode.

8 Claims, 12 Drawing Sheets

(56) References Cited

U.S. PATENT DOCUMENTS

| | | | |
|---|---|---|---|
| 2016/0128869 A1* | 5/2016 | Zacharias | A61M 1/80 |
| | | | 604/249 |
| 2017/0035454 A1* | 2/2017 | Yoshimine | A61B 17/32002 |
| 2017/0143369 A1* | 5/2017 | Downey | A61B 17/320068 |
| 2017/0274226 A1* | 9/2017 | Akagane | A61B 18/00 |
| 2019/0239916 A1* | 8/2019 | Yoshimine | H04R 17/10 |
| 2021/0236157 A1 | 8/2021 | Rhee et al. | |

* cited by examiner

ULTRASONIC HANDPIECE ASSEMBLY

FIELD

The present disclosure relates generally to ultrasonic handpieces used, for example, in cataract surgery to emulsify cataract tissue and aspirate the cataract tissue from the eye.

BACKGROUND

Historically, cataract surgery has been performed using ultrasonic handpieces providing a longitudinal or "jackhammer" like motion at a tip of a needle received by the handpiece. High-powered longitudinal mode ultrasonic handpieces used in cataract surgery typically consist of the components depicted in FIG. 1. The surgical needle threads into a stepped horn which is ultrasonically driven by a stack of piezoelectric ceramic elements. A spacer is located behind the stack of ceramic elements. A rear mass with a mount, isolation tube and Luer connector threads onto a center bolt which passes through the stack. When torqued, the rear mass applies a compressive pre-load to the stack. A lumen for aspiration of fragmented cataract tissue passes through the needle into the horn, through the center bolt and into the rear mass, exiting the Luer connector and passing into a flexible tube which is attached to a pump. O-ring bore seals, one located behind the horn step and the other in the rear mount, provide a water tight barrier for the handpiece inside its housing.

With longitudinal mode ("L mode") handpieces, cutting only occurs for the half of the oscillation cycle during which the needle tip advances toward the cataract. For the half of the cycle during which the needle tip moves away from the cataract, the needle tip is not cutting, but energy is required and heat is generated throughout the entire cycle. As a result, cutting efficiency is not optimized and cutting time is increased. The axial distance between the longitudinally retracted and extended positions of the needle tip during longitudinal vibrational motion is referred to as the "longitudinal stroke."

Torsional mode phacoemulsification was introduced by Alcon, Inc. in 2006 in the form of the OZil® handpiece, the internal assembly of which is depicted in FIG. 2. The OZil® handpiece delivers both longitudinal and torsional motion to the needle, which, depending upon the tip geometry, cuts in either a rotating or transverse shearing motion. Longitudinal vibration generated by the stack is partially converted to torsional motion by a torsional spring integrally machined into the horn of the OZil® handpiece assembly depicted in FIG. 2. A bent tip needle with a Kelman configuration amplifies the shaft torsion through a side-to-side pivoting motion at the tip while a needle with a straight or flared tip cuts with a rotational motion amplified by the distance from the center of the needle to the outermost cutting edge of the tip. When the needle tip is moving transversely or rotationally in torsional mode ("T mode"), more edge is applied to cutting as opposed to repulsing the cataract, and the needle tip maintains contact with the cataract throughout the cycle to cut more efficiently than purely L mode handpieces. The angular distance travelled by the needle tip from one side to the other during torsional vibrational motion is referred to as the "torsional stroke."

An improvement on the OZil® handpiece assembly is described in U.S. U.S. Pat. No. 8,395,299 (Bromfield), the entire disclosure of which is incorporated herein by reference. Unlike the OZil® handpiece assembly, in which the spring partially converting longitudinal motion to torsional motion is integral with the horn, the Bromfield design incorporates the spring into the handpiece assembly as a discrete component. This significantly enhances design flexibility by facilitating alternative configurations and alternative spring materials to achieve different performance objectives. FIG. 3 shows a prior art longitudinal-torsional (L-T) mode ultrasonic handpiece assembly developed by the applicant, Moog Inc., based on the Bromfield design. Like the OZil® handpiece assembly, the Moog L-T handpiece assembly provides ophthalmologists with the ability to switch between predominantly torsional and predominantly longitudinal modes of operation during cataract surgery.

SUMMARY

It is an object of the present disclosure to increase the torsional stroke of an ultrasonic L-T handpiece for a given electrical drive power to thereby improve performance of the L-T handpiece when it is operated in the T mode by a surgeon.

It is another object of the present disclosure to accomplish the aforementioned performance improvement while also making the L-T handpiece lighter and more compact, thereby enhancing ease of use during surgery.

In furtherance of these and other objects, an ultrasonic L-T handpiece assembly is disclosed. The handpiece assembly generally comprises a horn, a rear mass, a needle, a plurality of piezoelectric elements, and an L-T spring. The horn is elongated along a longitudinal axis and includes a rear end, a front end opposite the rear end, and a horn lumen extending axially through the horn. The rear mass, which may be threadably attached to the rear end of the horn, has a rear mass lumen extending axially through the rear mass and communicating with the horn lumen. The needle, which may be threadably attached to the front end of the horn, has a needle lumen extending axially through the needle and communicating with the horn lumen. The plurality of piezoelectric elements are arranged coaxially about the horn in a stack, and the L-T spring may be arranged coaxially about the horn adjacent to and axially behind the stack of piezoelectric elements.

The horn includes a low gain section axially in front of the stack of piezoelectric elements and a high gain section axially in front of the low gain section, wherein the high gain section has a cross-sectional area less than a cross-sectional area of the low gain section.

The ultrasonic handpiece assembly has a first L-T mode at a first resonant frequency, a T mode at a second resonant frequency, a second L-T mode at a third resonant frequency, and an L mode at a fourth resonant frequency. In accordance with the present disclosure, the low gain section of the horn includes a circumferential groove arranged at an axial location corresponding to a vibrational node of the first resonant L-T mode of the handpiece assembly. Frequency separation between a lower resonant frequency of the first L-T mode and a higher resonant frequency of the T mode results in torsional vibration of the first L-T mode interacting constructively with torsional vibration of the T mode, thereby increasing the torsional stroke of the ultrasonic handpiece assembly in the T mode.

BRIEF DESCRIPTION OF THE DRAWING VIEWS

The nature and mode of operation of the present disclosure will now be more fully described in the following detailed description taken with the accompanying drawing figures, in which.

Figure 1:
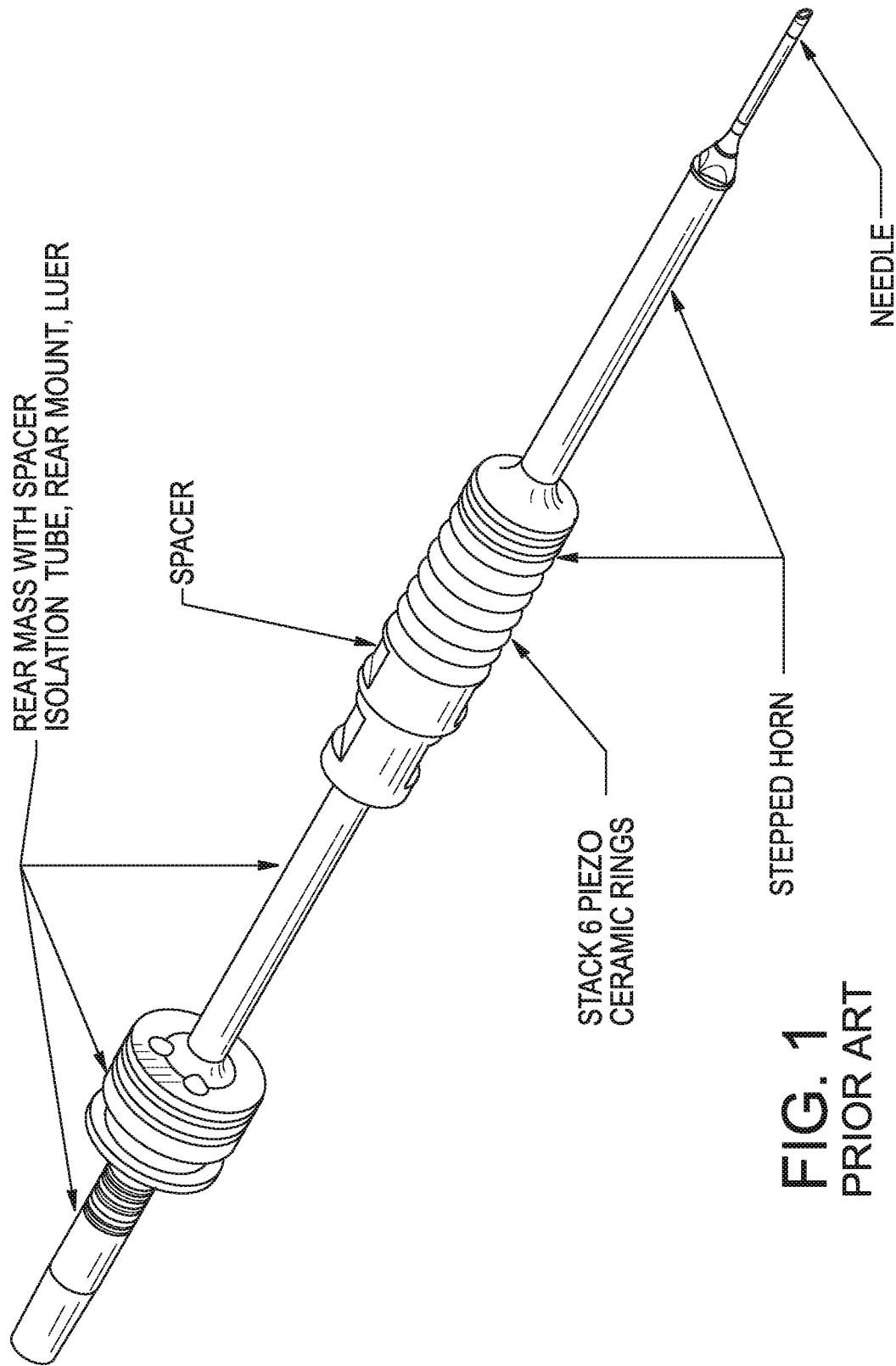
FIG. 1 is a perspective view of a longitudinal (L) mode ultrasonic handpiece assembly according to the prior art.
Figure 2:
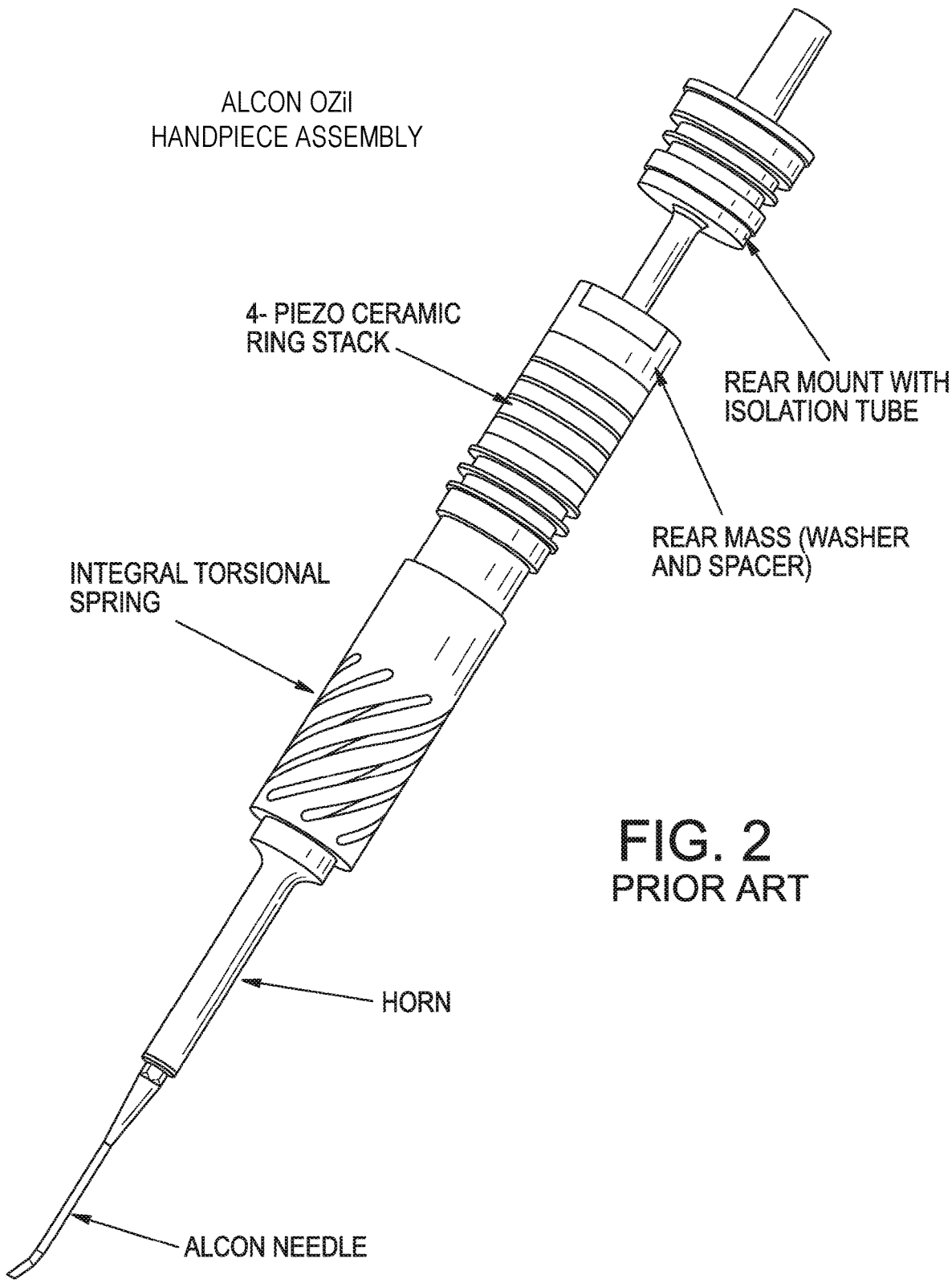
FIG. 2 is a perspective view of a longitudinal-torsional (L-T) mode ultrasonic handpiece assembly according to the prior art.
Figure 3:
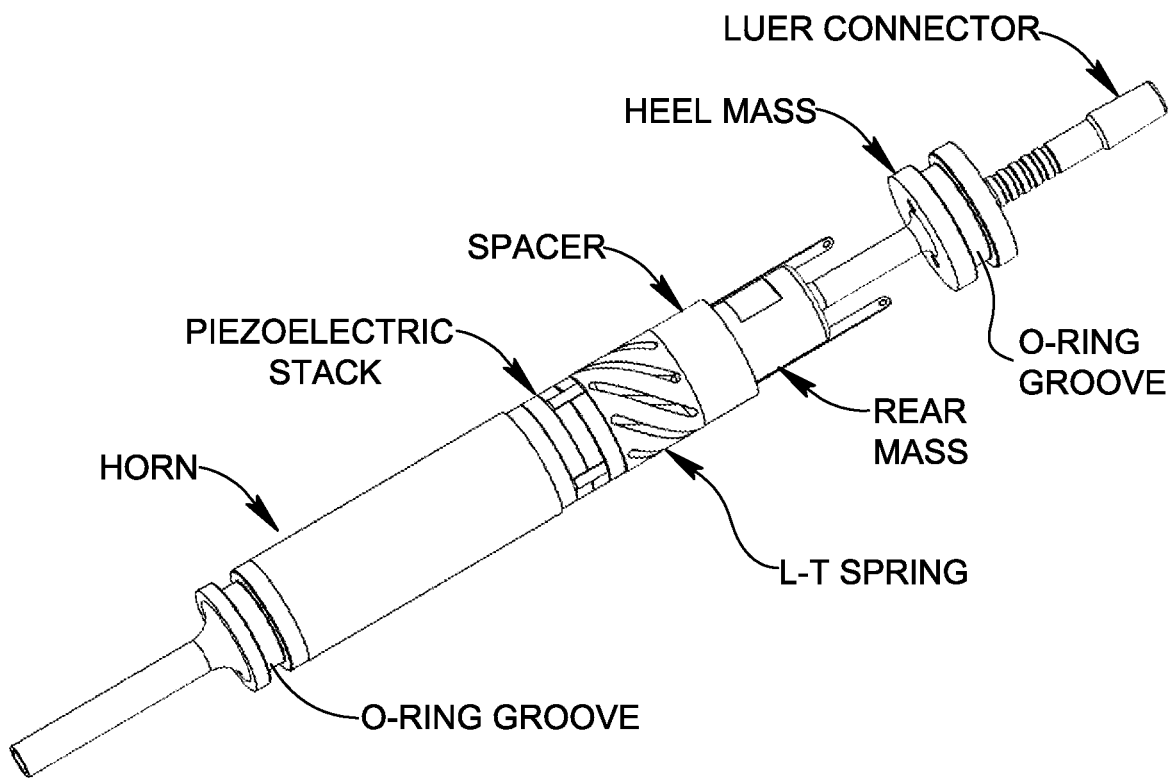
FIG. 3 is a perspective view of another L-T mode ultrasonic handpiece assembly according to the prior art.
Figure 14:
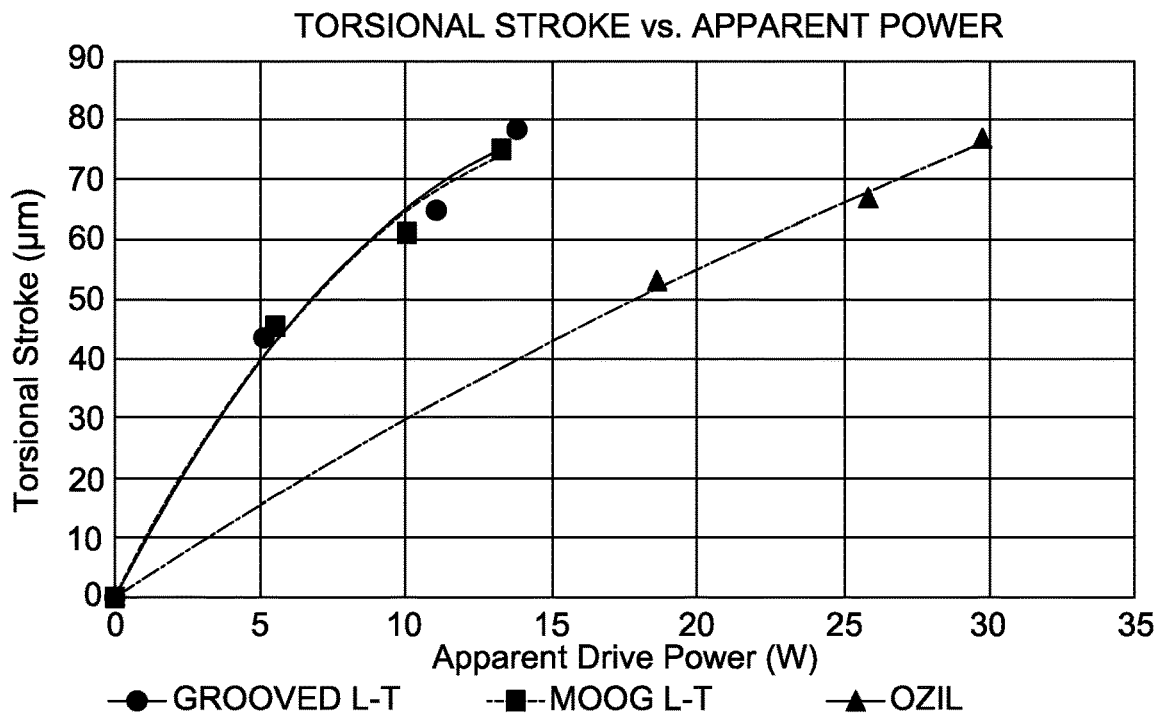
Figure 15:
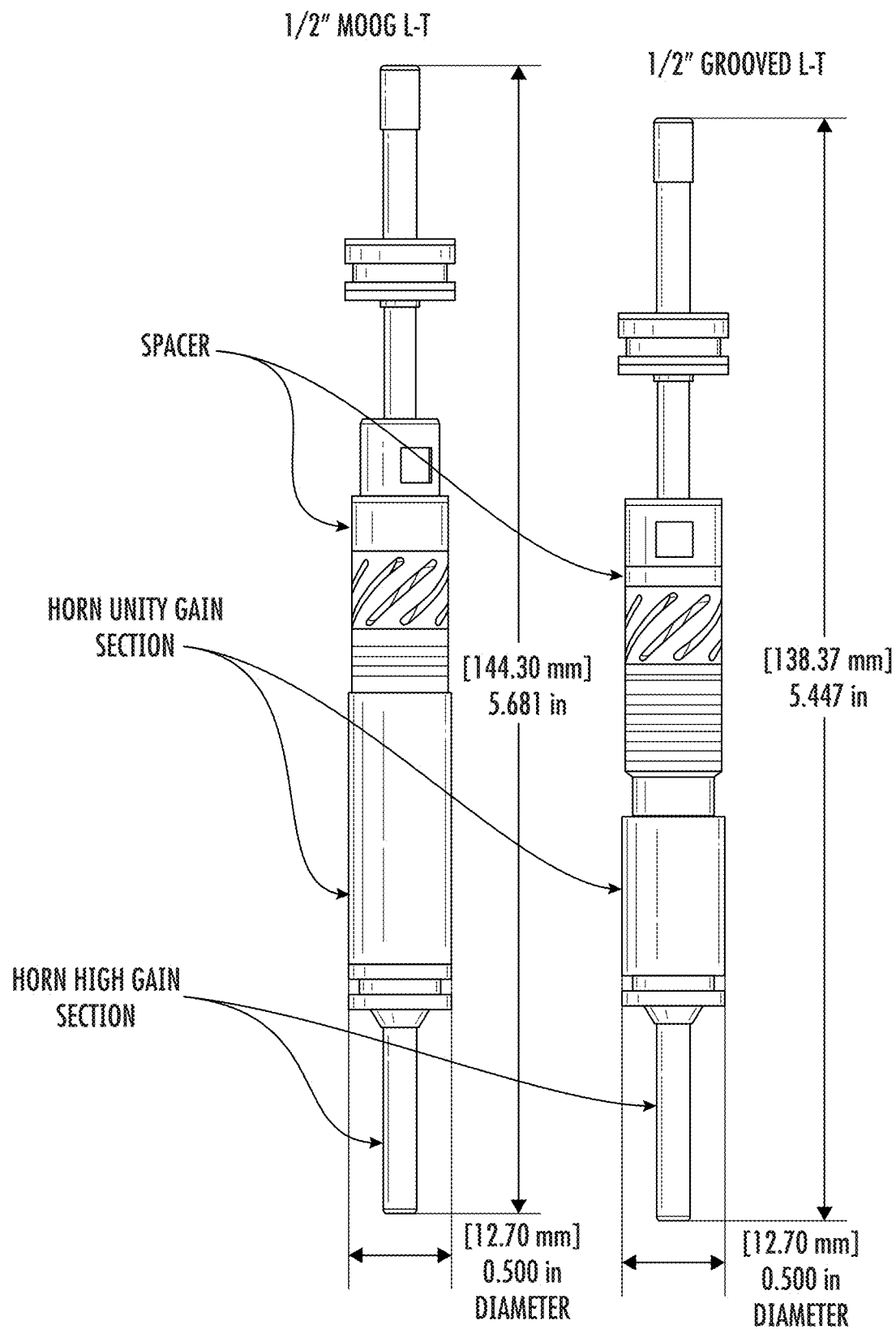

FIG. 14 is a plot of torsional stroke as a function of apparent drive power showing measurement results of high power testing conducted for the Alcon OZil® handpiece assembly shown FIG. 2, the Moog L-T handpiece assembly shown in FIG. 3, and a Grooved L-T handpiece assembly of the present disclosure; and FIG. 15 is an elevational view showing a grooved handpiece assembly of the present disclosure side-by-side in relation to the Moog L-T handpiece assembly of FIG. 3, wherein the handpiece assemblies are shown without needles;

DETAILED DESCRIPTION

Figure 4:
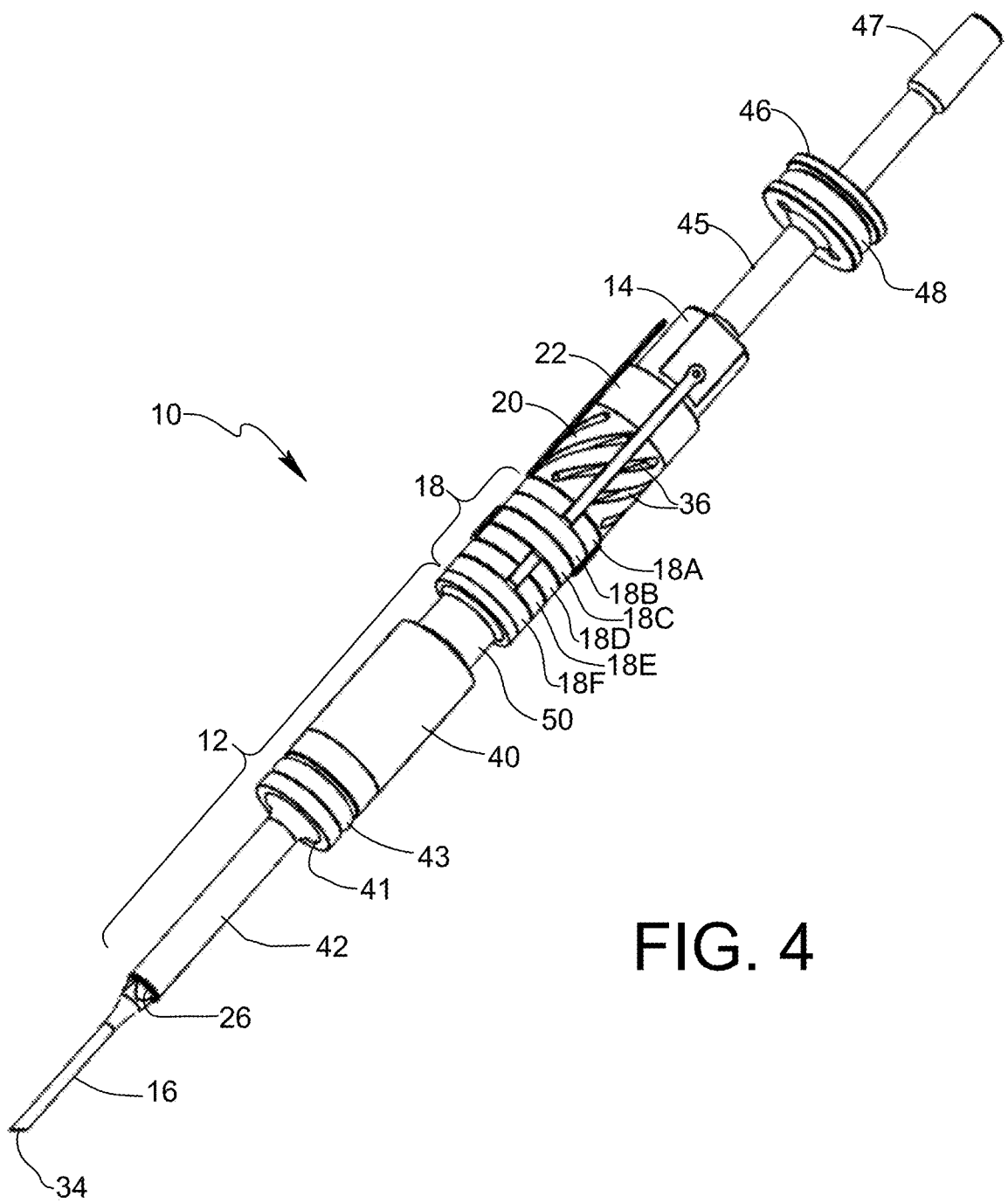
FIG. 4 is a perspective view of an L-T mode ultrasonic handpiece assembly according to an embodiment of the present disclosure.
Figure 5:
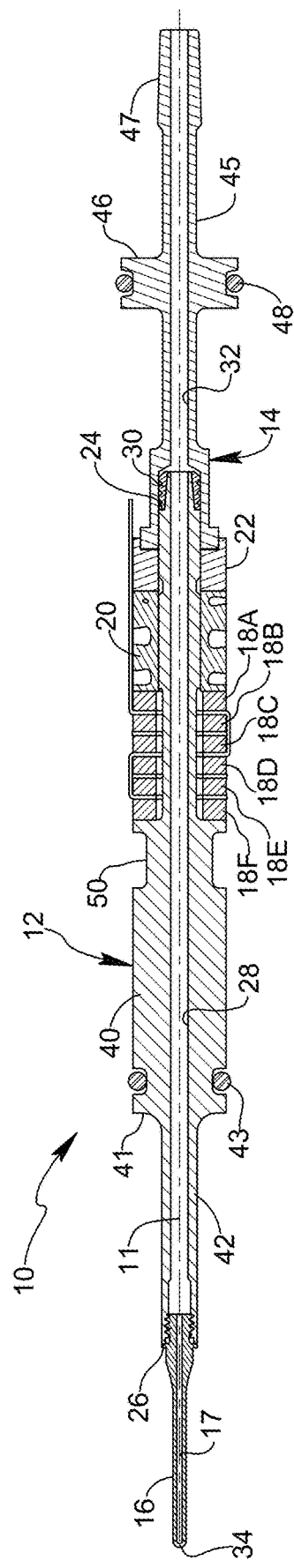
FIG. 5 is a longitudinal cross-sectional perspective view of the L-T mode ultrasonic handpiece assembly shown in FIG. 4.

FIGS. 4 and 5 show an L-T ultrasonic handpiece assembly 10 formed in accordance with an embodiment of the present disclosure. Handpiece assembly 10 may generally comprise a horn 12, a rear mass 14, a needle 16, a plurality of piezoelectric elements 18A-18F, an L-T spring 20, and a spacer 22.

Horn 12 is elongated along a longitudinal axis 11 and includes a rear end 24, a front end 26 opposite the rear end, and a horn lumen 28 extending axially through the horn. Rear mass 14 may be attached to rear end 24, for example by mating attachment threads and/or by a frictionally engaged seal 30, and has a rear mass lumen 32 extending axially through the rear mass and communicating with horn lumen 28. Needle 16 may be attached to front end 26 of horn 12 by threaded coupling, and has a needle lumen 17 extending axially through the needle and communicating with horn lumen 28. The plurality of piezoelectric elements 18A-18F are arranged coaxially about horn 12 in a stack 18. The piezoelectric elements 18A-18F are electrically connected in parallel and convert alternating electrical drive voltage into longitudinal vibrational motion at the frequency of the alternating drive voltage. Piezoelectric elements 18A-18F may be, for example, piezoelectric ceramic rings such as PZT8 ceramic rings. L-T spring 20 may be arranged coaxially about horn 12 adjacent to and axially behind the stack 18 of piezoelectric elements 18A-18D, and is configured to convert oscillatory longitudinal drive motion generated by piezoelectric stack 18 to both longitudinal and torsional motion at a tip 34 of needle 16. For example, L-T spring 20 may include a plurality of helical groves 36 formed in an outer cylindrical surface of the L-T spring body. Grooves 36 may be produced in a manner similar to straight grooves by rotating needle L-T spring 20 as the grooves are being formed. Additional and/or alternative aspects and details of L-T spring 20 are described in the aforementioned U.S. Pat. No. 8,395,299 to Bromfield. Horn 12 mechanically amplifies the resonant vibrational motion, both torsional and longitudinal, generated by piezoelectric stack 18 and L-T spring 20. The motion produced at needle tip 34 is used, for example, to emulsify a cataract during surgery for removal. Spacer 22 axially behind L-T spring 20 may be used to adjust the length of assembly 10 and thereby vary the resonant frequencies of the torsional and longitudinal vibration modes.

Horn 12 includes a low gain section 40 axially in front of the stack 18 of piezoelectric elements 18A-18D, and a high gain section 42 axially in front of the low gain section 40. High gain section 42 has a transverse cross-sectional area (i.e., a cross-sectional area viewed in a direction of longitudinal axis 11) that is less than a transverse cross-sectional area of low gain section 40. Low gain section 40 and high gain section 42 may be cylindrical in shape, and a radial step 41 may provide a transition between low gain section 40 and high gain section 42. Low gain section 40 may have a circumferential groove configured to hold a compliant O-ring fluid seal 43 proximate an axial location of radial step 41.

Horn 12 may have a center bolt 44 extending rearwardly from low gain section 40 and passing through aligned openings in piezoelectric elements 18A-18F, L-T spring 20, and spacer 22. Center bolt 44 may thread into rear mass 14, whereby a torsional load applied to the rear mass generates compressive pre-stress which holds piezoelectric stack 18 together. Compressive pre-stress is necessary in high power handpiece assemblies to prevent dynamic tensile stress from exceeding the tensile strength of the ceramic piezoelectric elements 18A-18F and fracturing the ceramic piezoelectric elements.

Assembly 10 may further include an isolation tube 45, a heel mass 46, and a tapered Luer connector 47 integral with rear mass 14. Heel mass 46 may have a circumferential groove for receiving a radial spring or compliant O-ring fluid seal 48. Luer connector 47 allows flexible medical grade tubing (not shown) to be attached to assembly 10 in fluid communication with an aspiration lumen collectively defined by needle lumen 17, horn lumen 28, and rear mass lumen 32. The aspiration lumen enables aspiration of a fragmented cataract through assembly 10 exiting the Luer connector 47 into attached medical grade tubing. Heel mass 46 in combination with Luer connector 47 vibrate with isolation tube 45 at a much lower resonant frequency than the resonant frequencies of the torsional and longitudinal modes. Consequently, rear mass 14 acts as a spring mass vibration isolation system for which vibrational nodes for the T mode and L mode of assembly 10 are nearly coincident at heel mass 46 and radial spring/O-ring 48, which may serve as an aft mount at which assembly 10 may be mounted to an external housing (not shown). In addition to the mentioned vibrational nodes for the aft mount location, there are vibrational nodes for the T mode and L mode nearly coincident at O-ring 43, which may serve as forward mount at which assembly 10 may be mounted to the external housing. The aft mount and forward mount locations corresponding to vibrational nodes provide locations at which the handpiece assembly may be mounted to the external housing to eliminate or significantly reduce dissipation of vibrational energy arising from damping. A central vibrational node may be located inside the stack of piezo-ceramic elements, where local strain is highest, to maximize vibration amplitude.

Horn 12, a rear mass 14, a needle 16, L-T spring 20, and spacer 22 may be manufactured as metal components, for example from titanium alloy Ti-6Al-4V providing biocompatibility, good spring and fatigue characteristics, and a high stiffness to density ratio. Alternate materials for horn 12, rear mass 14, L-T spring 20, and spacer 22 include aluminum alloy, stainless steel and beryllium copper. Of course, other suitable materials may be used without straying from the present disclosure.

In one embodiment, the low gain section 40 of horn 12 is ½ inch in diameter and 1.16 inches in length; the high gain section 42 of horn 12 is 0.15 inches in diameter and 1.13 inches in length; piezoelectric elements 18A-18F are ring-shaped ceramic elements having an outer diameter of ½-inch, an inner diameter of 0.197 inches, and an axial thickness (i.e., length) of 0.08 inches; and spacer 22 is ½-inch in diameter and 0.11 inches in length.

In another embodiment, the low gain section 40 of horn 12 is ⅜-inch in diameter and 1.16 inches in length; the high gain section 42 of horn 12 is 0.14 inches in diameter and 0.915 inches in length; piezoelectric elements 18A-18F are ring-shaped ceramic elements having an outer diameter of ⅜-inch, an inner diameter of 0.193 inches, and an axial thickness (i.e., length) of 0.08 inches; and spacer 22 is ⅜-inch in diameter and 0.21 inches in length.

As may be seen in FIGS. 4 and 5, the low gain section 40 of horn 12 includes a circumferential groove 50. In accordance with the present disclosure including details described below, groove 50 is located and configured to increase a torsional stroke of handpiece assembly 10 in a T mode thereof.

Figure 6:
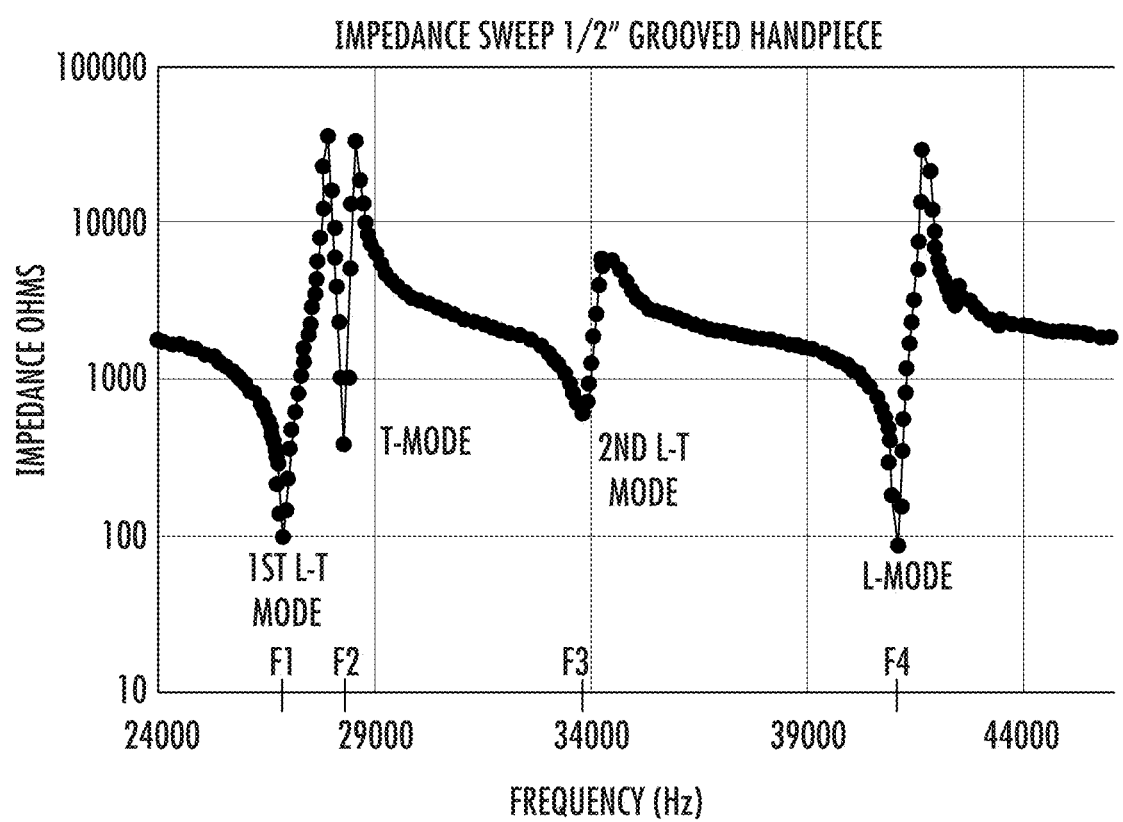
FIG. 6 is a graph illustrating a low power impedance sweep of the handpiece assembly of FIG. 4.

Attention is now directed to FIG. 6 showing impedance as a function of frequency as measured during a low power impedance sweep of handpiece assembly 10. As may be seen, handpiece assembly 10 has a first L-T mode at a first resonant frequency F1, a T mode at a second resonant frequency F2, a second L-T mode at a third resonant frequency F3, and an L mode at a fourth resonant frequency F4. In the graph of FIG. 6, first resonant frequency F1 corresponding to the first L-T mode is approximately 26.9 kHz, second resonant frequency F2 corresponding to the T mode is approximately 28.3 kHz, third resonant frequency F3 corresponding to the second L-T mode is approximately 33.8 kHz, and fourth resonant frequency F4 corresponding to the L mode is approximately 41.0 kHz. Vibrational motion for the first L-T mode and the second L-T mode is distributed over the entire length of the handpiece assembly. Operational modes for cataract surgery are the T mode and the L mode. The predominantly torsional vibrational mode (T mode) is driven at second resonant frequency F2 and the predominantly longitudinal vibrational mode (L mode) is driven at fourth resonant frequency F4 that is separate from second resonant frequency F2.

For reasons explained below, circumferential groove 50 is arranged at an axial location corresponding to a vibrational node of the first L-T mode of handpiece assembly 10 and may be configured such that torsional vibration of the first L-T mode of handpiece assembly 10 interacts constructively with torsional vibration of the T mode of handpiece assembly 10 to increase a torsional stroke of the handpiece assembly in the T mode.

The inventor has determined that for a T mode frequency F2 exceeding the 1st L-T mode frequency F1 by approximately 1.3 to 2.2 kHz, constructive interaction occurs between the T mode vibration and the first L-T mode vibration, thereby increasing torsional stroke in the T mode. The inventor has further determined that when the T mode frequency F2 is less than the first L-T mode frequency F1, interaction between the T mode vibration and the first L-T mode vibration is destructive and torsional stroke in the T mode decreases.

Figure 7:
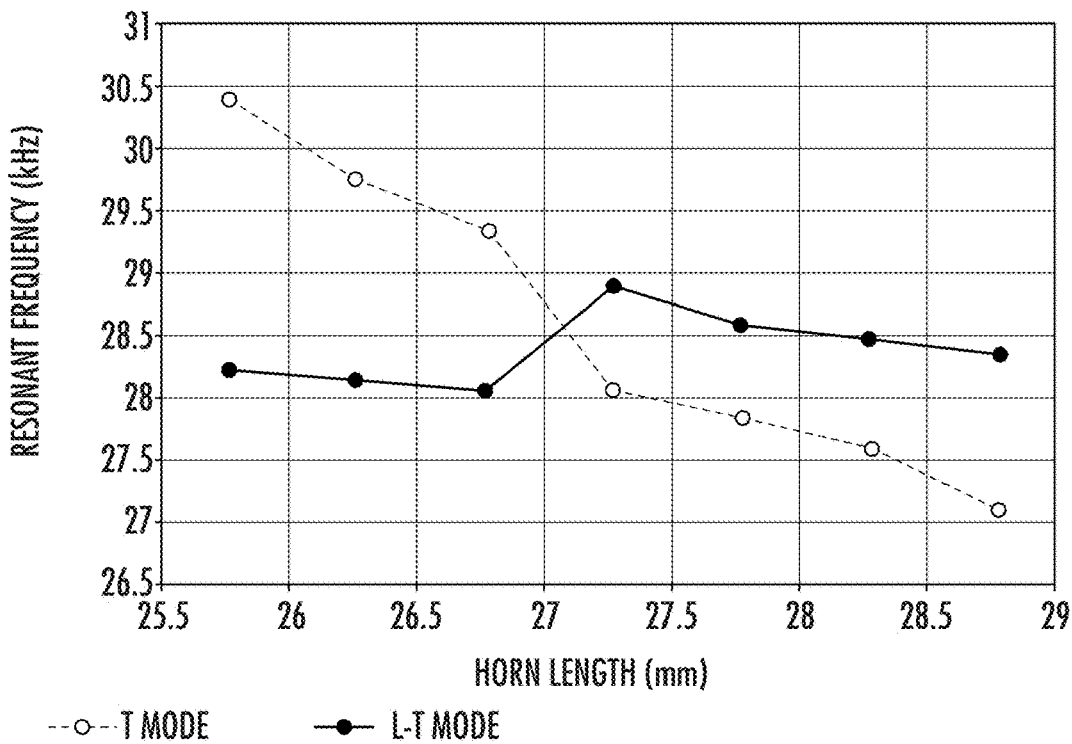
FIG. 7 is a plot of resonant frequency as a function of horn length for the first L-T mode and T mode of the prior art handpiece assembly shown in FIG. 3.

The resonant frequency F1 of the first L-T mode and the resonant frequency F2 of the T mode are dependent in part on the geometry of the horn. For example, FIG. 7 demonstrates that as the axial length of the horn increases, the T mode frequency F2 decreases from roughly 30.5 kHz to about 27 kHz. FIG. 7 also demonstrates that for the same increase in the horn length, there is significantly less change in the resonant frequency F1 of the first L-T mode. The T mode resonant frequency F2 starts out roughly 2.2 kHz above the first L-T mode resonant frequency F1. At a horn length of about 27.1 mm, the T mode resonant frequency F2 crosses over the first L-T mode resonant frequency F1, falling below and diverging from the first L-T mode resonant frequency F1 as the horn length further increases.

Figure 8:
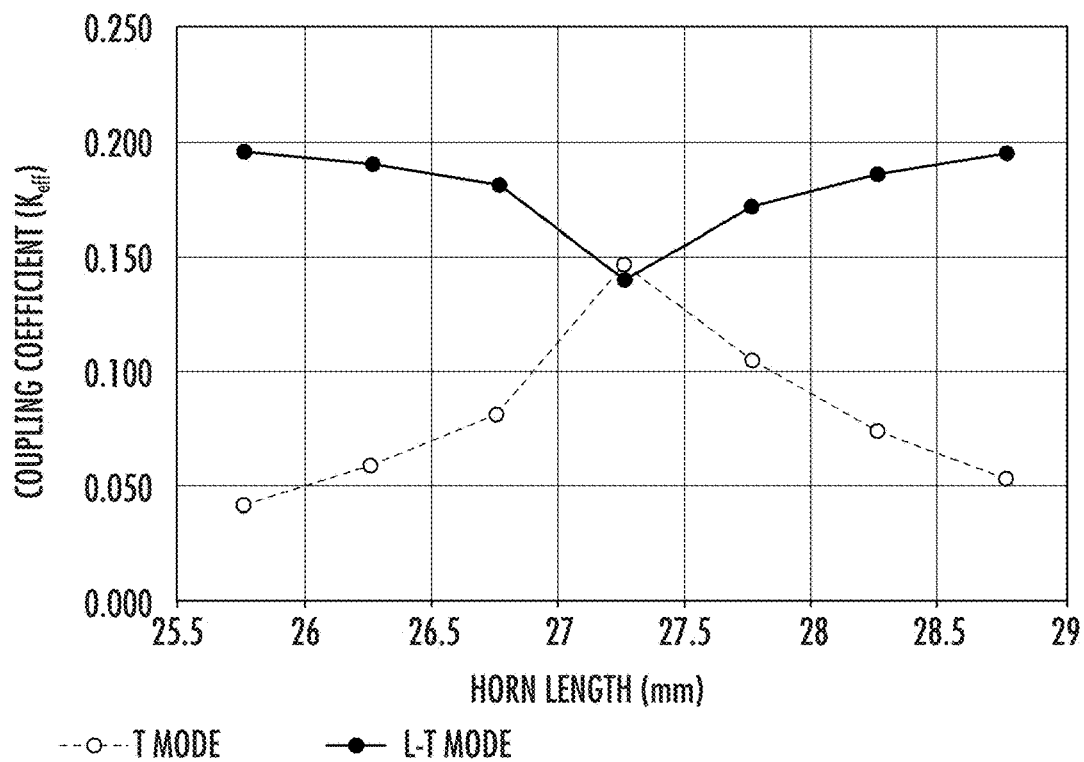
FIG. 8 is a plot of effective coupling ($K_{eff}$) as a function of horn length for the first L-T mode and T mode of the prior art handpiece assembly shown in FIG. 3.

FIG. 8 depicts the effect that increasing horn length has upon effective coupling ($K_{eff}$) for the T mode and first L-T mode. Effective coupling $K_{eff}$ is calculated as follows:

$$K_{eff} = \sqrt{1 - (f_R/f_{AR})^2} = \sqrt{\frac{\text{converted mechanical energy}}{\text{input electrical energy}}}$$

where $f_R$ and $f_{AR}$ are the resonant and anti-resonant frequencies for the active resonant modes plotted, for example, in FIG. 6. The effective coupling $K_{eff}$ represents the capability of a handpiece assembly having piezoelectric transducer elements to convert electrical energy into mechanical energy and vice versa. For L-T handpieces, electrical power in the form of a drive voltage is converted to mechanical power in the form of vibrational motion. Taken together, FIGS. 7 and 8 show that, for a T mode frequency F2 higher than a first L-T mode frequency F1, as the difference in frequency between the T mode and the first L-T mode decreases, interaction between these modes increases and effective coupling for the T mode increases and reaches a maximum when the two modes merge.

Figure 9:
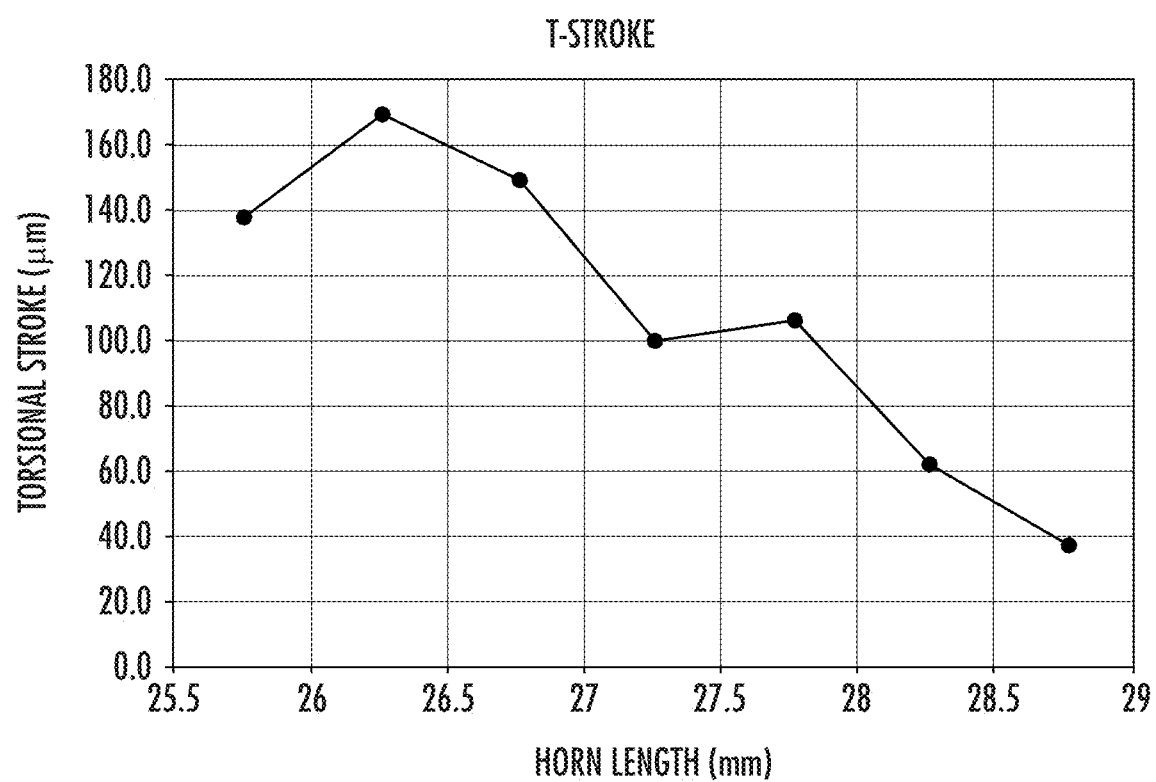
FIG. 9 is a plot of torsional stroke as a function of horn length for the T mode of the prior art handpiece assembly shown in FIG. 3.

Reference is now made to FIG. 9 in conjunction with FIG. 7. While maximum effective coupling is achieved by conversion of low drive voltage into high vibrational motion, FIGS. 7 and 9 demonstrate that the best performance corresponding to peak torsional stroke occurs for a T mode resonant frequency F2 which is roughly 1.6 kHz higher than the first L-T mode resonant frequency F1. FIGS. 7 and 9 also demonstrate that torsional stroke is high, 140 µm or more, for the T mode resonance frequency F2 exceeding the first L-T mode resonance frequency F1 by 1.3 kHz to 2.2 kHz. However, at a horn length of roughly 27.1 mm, the T mode resonant frequency F2 falls below the first L-T mode resonant frequency F1 and the torsional stroke decreases significantly and continues to decrease as the horn length increases and the T mode resonance frequency decreases. This indicates that when the T mode resonance frequency F2 exceeds the first L-T mode resonance frequency F1 by approximately 1.3 kHz to 2.2 kHz, constructive interaction occurs between the T mode and first L-T mode increasing torsional stroke. It also indicates that when the T mode resonance frequency F2 is less than the first L-T mode resonance frequency F1, the T mode interaction with the first L-T mode is destructive and decreases the torsional stroke.

The grooved handpiece depicted in FIGS. 4 and 5 employs this unique interaction between the T mode and the first L-T mode by positioning circumferential groove 50 in horn 12 at an axial location corresponding to a vibrational node of the first L-T mode, and varying the depth of the groove instead of varying the horn length in order to adjust the first L-T mode resonance frequency F1 relative to the T mode resonance frequency F2.

Figure 10:
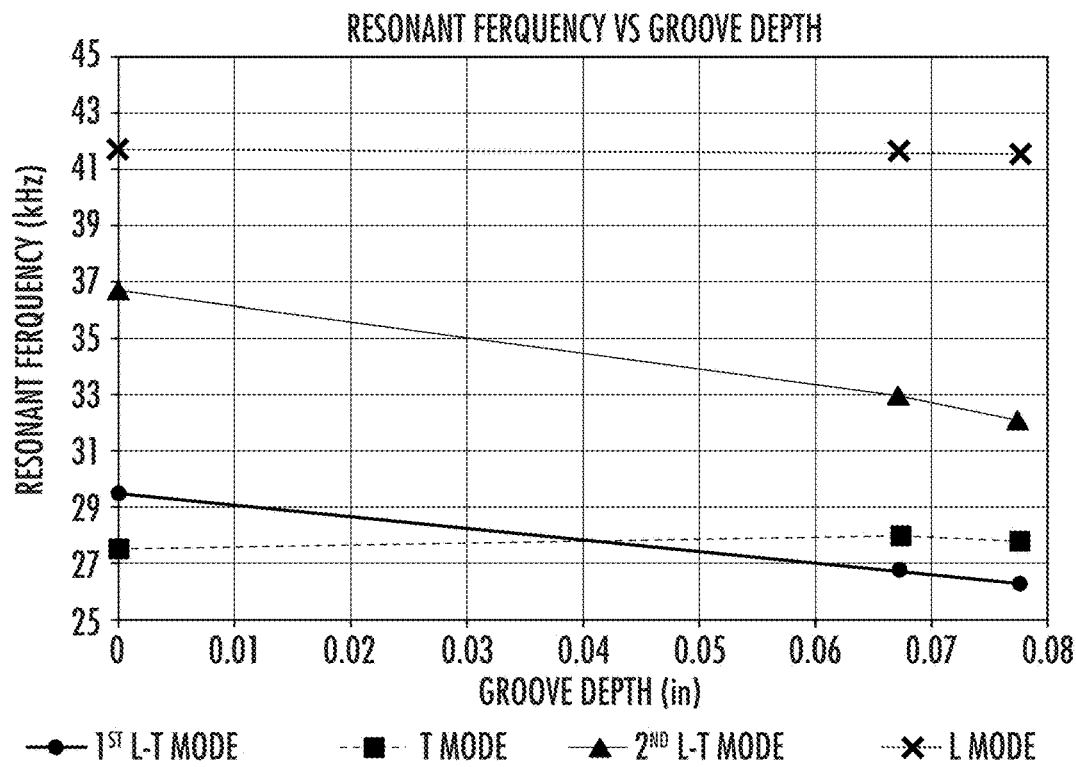
FIG. 10 is a plot of resonant frequency as a function of groove depth for the first L-T mode, T mode, second L-T mode, and L mode of a grooved L-T handpiece assembly according to the present disclosure.

The effect that groove 50 in horn 12 has upon performance of handpiece assembly 10 was analyzed using finite element models in which the cylindrical low gain section 40 of horn 12 was specified with a ½-inch diameter and other dimensions of the ½-inch diameter embodiment described above. As mentioned, groove 50 is deliberately positioned coincident with a vibrational node of the first L-T mode where vibrational amplitude is at a minimum. A width of groove 50 along axis 11 was specified at 0.22 inches. The groove depth may be varied to adjust the resonant frequency F1 of the first L-T mode relative to the resonant frequency F2 of the T mode as illustrated by FIG. 10. The resonant frequency F1 for the first L-T mode and resonant frequency F3 for the second L-T mode decrease significantly with increasing groove depth, whereas the respective resonant frequencies F2 and F4 of the T mode and L mode undergo little change as groove depth increases. Thus, by varying the depth of groove 50, it is possible to adjust the first L-T mode resonant frequency F1 relative to the T mode resonant frequency F2.

Figure 11:
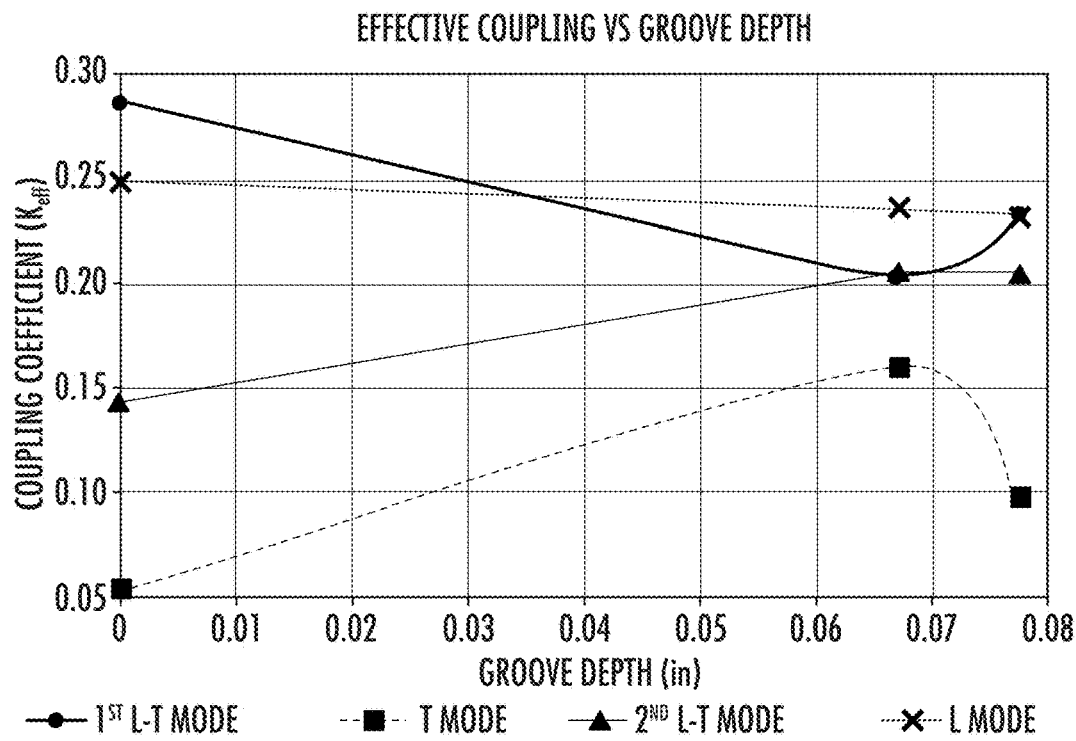
FIG. 11 is a plot of effective coupling ($K_{eff}$) as a function of groove depth for the first L-T mode, T mode, second L-T mode, and L mode of a grooved L-T handpiece assembly according to the present disclosure.

Reference is now made to FIG. 11 in conjunction with FIG. 10. No groove (i.e., groove depth=0) results in the T mode resonant frequency F2 being approximately 2000 Hz less than the first L-T mode resonant frequency F1, and a low effective coupling coefficient $K_{eff}$ of 0.05 is realized. A groove depth of 0.07 inch (1.8 mm) results in a frequency difference of approximately 1.4 kHz between the T mode resonant frequency F2 and the first L-T mode resonant frequency F1, which is within the preferred range between 1.3 kHz through 2.2 kHz with the first L-T mode frequency lower than the T mode frequency. Effective coupling $K_{eff}$ for the T mode is significantly increased from 0.05 for no groove to approximately 0.16 for a groove depth of 0.07 inch. Further increasing the groove depth to 0.078 inch increases separation between T mode resonant frequency F2 and first L-T mode resonant frequency F1, and the effective coupling $K_{eff}$ drops to 0.10. Resonant frequency separation with the T mode frequency F2 higher than the first L-T mode frequency F1 results in torsional vibration of the first L-T mode interacting constructively with torsional vibration of the T mode.

Figure 12:
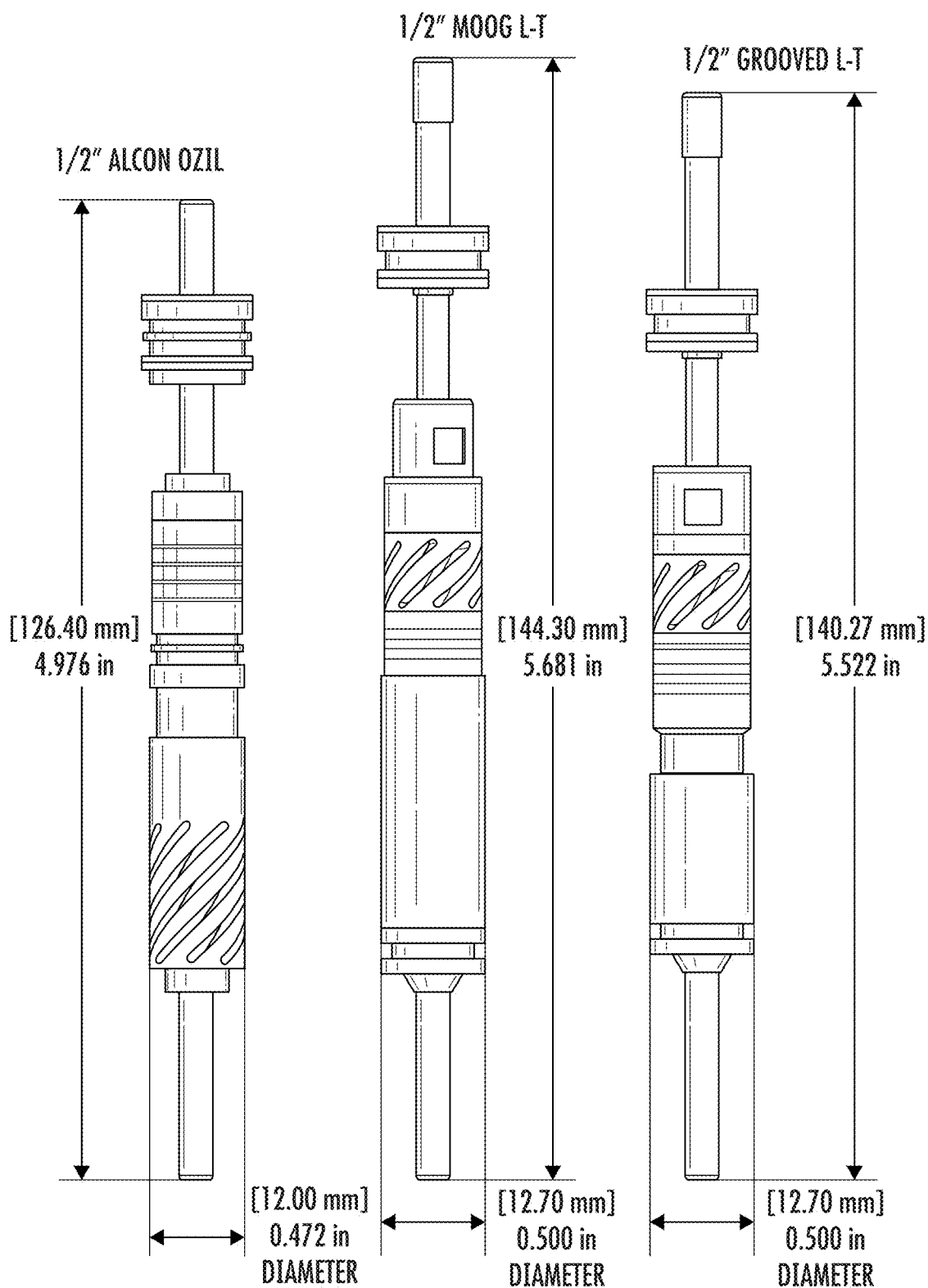
FIG. 12 is an elevational view showing an Alcon OZil® handpiece assembly of the prior art, a Moog L-T handpiece assembly of the prior art, and a Grooved L-T handpiece assembly according to the present disclosure as tested by applicant, wherein the handpiece assemblies are shown without needles.

Based upon the analysis of finite element models described above, a prototype embodiment of ultrasonic handpiece assembly 10 having a ½-inch diameter low gain horn section with a 0.07 inch deep groove ("Grooved L-T" assembly) was tested against the Alcon OZil® handpiece assembly shown in FIG. 2 and the Moog L-T handpiece assembly shown in FIG. 3. The tested Alcon OZil® and Moog L-T handpiece assemblies also comprised a horn having a low gain section that is ½ inch in diameter. The Alcon OZil® and Moog L-T assemblies each have four PZT8 ceramic rings, whereas the Grooved L-T assembly has six PZT8 ceramic rings. Low and high power tests were performed for the OZil® handpiece assembly with Alcon's 21 gauge bent tip needle attached, and for the ½-inch Moog L-T and ½-inch Grooved L-T handpiece assemblies each with a 19 gauge straight needle having a 30° beveled cutting tip. These needles are frequently selected by surgeons for use with these handpieces. The tested handpiece assemblies are shown side-by-side in FIG. 12, without attached needles.

Low Power Testing:

Testing began with low power impedance sweeps over frequency to measure and compare key performance characteristics of piezoelectric transducer handpiece assemblies. Characteristics of the transducer resonant modes obtained from the sweeps include resonant frequency ($f_R$) at minimum impedance ($Z_{min}$) and anti-resonant frequency ($f_{AR}$) at maximum impedance ($Z_{max}$), and the effective coupling coefficient ($K_{eff}$) for the stack resonant modes is computed using the equation set forth above. Data from the lower power impedance sweeps was also used to compute a mechanical quality factor $Q_M$ representing the vibrational stroke amplitude boost arising from resonance. Typically, if drive voltage is limited, a larger quality factor increases vibration amplitude. The product of mechanical quality factor $Q_M$ and the square of the effective coupling coefficient $K_{eff}$ is a useful figure of merit ("FOM") characterizing resonance strength and the capability of piezoelectric transducers to convert electrical power to mechanical power. In addition, low frequency capacitance is also measured during low power impedance sweeps.

Results from these sweeps for each of the handpiece assemblies are set forth in Table 1:

TABLE 1

Low Power Testing Results

| MODE | PARAMETER | Alcon OZil L-T (OZil needle) | Moog L-T (19G straight needle) | Grooved L-T (19G straight needle) |
|---|---|---|---|---|
| T Mode | Resonant Frequency [Hz] | 31397 | 30156 | 28282 |
|  | Anti-Resonant Frequency [Hz] | 31423 | 30244 | 28545 |
|  | Effective Coupling ($K_{eff}$) | 0.041 | 0.076 | 0.136 |
|  | Minimum Impedance [Ohms] | 621 | 176 | 148 |
|  | Mechanical Q ($Q_M$) | 480 | 2503 | 2571 |
|  | FOM | 0.81 | 14.46 | 47.55 |
|  | Capacitance [Pf] | 2791 | 2148 | 2597 |
| L Mode | Resonant Frequency [Hz] | 44066 | 42590 | 41041 |
|  | Anti-Resonant Frequency [Hz] | 44605 | 42822 | 41710 |
|  | Effective Coupling ($K_{eff}$) | 0.155 | 0.104 | 0.178 |
|  | Minimum Impedance | 61 | 107 | 79 |

TABLE 1-continued

Low Power Testing Results

| MODE | PARAMETER | Alcon OZil L-T (OZil needle) | Moog L-T (19G straight needle) | Grooved L-T (19G straight needle) |
|---|---|---|---|---|
| | [Ohms] | | | |
| | Mechanical Q ($Q_M$) | 286 | 1498 | 733 |
| | FOM | 6.87 | 16.20 | 23.22 |
| | Capacitance [pF] | 2791 | 2148 | 2571 |
| | Frequency Ratio (L/T) | 1.40 | 1.41 | 1.45 |
| First L-T Mode | Resonant Frequency [Hz] | 26052 | 27826 | 26865 |
| | Anti-Resonant Frequency [Hz] | 26224 | 28451 | 27900 |
| | Freq. Separation T to $1^{st}$ L-T [Hz] | 5345 | 2330 | 1417 |

The first L-T mode for the OZil® handpiece assembly has a resonant frequency 5345 Hz less than the resonant frequency of the T mode, which is considerably beyond the preferred range of 1.3 kHz to 2.2 kHz for constructive interaction between these modes which increases torsional stroke. For the Moog L-T handpiece assembly, the T mode to first L-T mode resonant frequency separation is 2330 Hz, which is slightly outside the preferred range for constructive interaction. For the Grooved L-T handpiece assembly, groove placement and depth produce T mode to first L-T mode resonant frequency separation of 1417 Hz, which is within the preferred range, with the T mode resonant frequency higher than the first L-T mode resonant frequency. This results in constructive interaction, thereby increasing torsional stroke and improving T mode performance.

As evidenced by Table 1, the mechanical quality factor $Q_M$ and the effective coupling coefficient $K_{eff}$ of the OZil® assembly are much lower than for the Moog L-T and Grooved L-T assemblies. Effective coupling for the Moog L-T is also about half the effective coupling for the Grooved L-T. The FOM value for OZil® at 0.8 is significantly less than for Moog L-T at 14.5 and both are far less than the FOM for the Grooved L-T of 47.6. The minimum impedance $Z_{min}$ of the Grooved L-T at T mode resonance (148Ω) is also significantly lower than the $Z_{min}$ for the OZil® (621Ω) and for the Moog L-T (176 Ω). Due to resonant frequency spacing between the T mode and first L-T mode which falls within the preferred range for constructive interaction as a result of positioning groove 50 at an axial location corresponding to a vibrational node of the first L-T mode and deliberately selecting the groove depth, the Grooved L-T handpiece assembly achieves superior low power T mode performance characteristics when compared to the Moog L-T assembly and in particular when compared to the Alcon OZil® assembly.

Low power L mode performance for all three ½-inch handpiece assemblies is similar with exception of the L mode resonant frequencies, which are 41000 Hz for the Grooved L-T assembly, 42590 Hz for Moog L-T assembly, and 44000 for the OZil® assembly. Groove position and depth do not significantly affect the L-mode. Effective coupling for all three is similar, with the Grooved L-T assembly having the highest at 0.178. Mechanical quality factor $Q_M$ for OZil® is 286, which is significantly below the mechanical quality factors $Q_M$ for the Moog L-T and Grooved L-T assemblies, which are 1498 and 733, respectively. Combining $Q_M$ and $K_{eff}$ in the FOM, the Grooved L-T assembly has the highest at 23.2, the OZil® assembly has the lowest at 6.9, and the Moog L-T assembly is in between at 16.2. The OZil® assembly has the lowest L mode minimum impedance at 61Ω, the Moog L-T assembly has the highest L mode minimum impedance at 107Ω, and the Grooved L-T assembly has an L mode minimum impedance that is in between the other two at 79Ω. While L-mode performance for all three handpiece assemblies is similar, the FOM for the Grooved L-T assembly is highest of the three and the respective minimum impedances of the Grooved L-T and Moog L-T assemblies are both less than that of the OZil® assembly.

High Power Testing:

High power stroke measurements for the T-mode and L-mode for all three ½-inch handpiece assemblies are compared next. High power performance characteristics for the T mode and L mode are listed in Table 2 below. T-stroke and L-stroke results in Table 2 were measured at roughly 5 W of power for each of the ½-inch handpiece assemblies. The measurements shown in parenthesis were scaled to exactly 5 W of power for direct comparison. The same needle was used with each handpiece assembly for high power testing as had been used for low power testing.

TABLE 2

High Power Testing Results

| MODE | PARAMETER | Alcon OZil L-T (OZil needle) | Moog L-T (19G straight needle) | Grooved L-T (19G straight needle) |
|---|---|---|---|---|
| T Mode | Real Drive Power [W] | 5.4 (5.0) | 5.45 (5.0) | 5.2 (5.0) |
| | Apparent Drive Power [W] | 22.5 (20.83) | 5.51 (5.05) | 5.25 (5.51) |
| | Resonant Frequency [Hz] | 31424 | 30173 | 28200 |
| | Current $I_{RMS}$ [mA] | 126 | 69 | 66 |
| | Voltage $V_{RMS}$ [V] | 180 | 79.8 | 79 |
| | Impedance [Ohms] | 1430 | 1157 | 1200 |
| | Power Factor | 0.24 | 0.99 | 0.99 |
| | Torsional Stroke (T Stroke) [µm] | 44 (42.3) | 45.3 (43.4) | 43.6 (42.75) |
| | T Stroke/$V_{RMS}$ | 0.24 (0.235) | 0.56 (0.54) | 0.55 (0.54) |
| | Longitudinal Stroke (L Stroke) [µm] | 8.6 | 4 | 6 |
| L Mode | Real Drive Power [W] | 5.1 (5.0) | 5.1 (5.0) | 5.1 (5.0) |
| | Apparent Drive Power [W] | 8.4 (8.2) | 6.5 (6.4) | 5.67 (5.55) |
| | Resonant Frequency [Hz] | 44122 | 42487 | 40890 |

TABLE 2-continued

High Power Testing Results

| MODE | PARAMETER | Alcon OZil L-T (OZil needle) | Moog L-T (19G straight needle) | Grooved L-T (19G straight needle) |
|---|---|---|---|---|
| | Current $I_{RMS}$ [mA] | 137 | 89 | 108 |
| | Voltage $V_{RMS}$ [V] | 60.3 | 74 | 52 |
| | Impedance [Ohms] | 439 | 831 | 482 |
| | Power Factor | 0.61 | 0.78 | 0.9 |
| | Longitudinal Stroke (L Stroke) [μm] | 27.6 (27.3) | 31 (30.7) | 29 (28.7) |
| | L Stroke/$V_{RMS}$ | 0.46 (0.45) | 0.42 (0.41) | 0.56 (0.55) |
| | Torsional Stroke (T Stroke) [μm] | 6.5 | 5.7 | 9 |

In addition to the 5 W measurements which produced the results in Table 2, high power T-stroke and L-stroke measurements were also performed at a real power of roughly 10 W and at the real power which produces 75 μm T-stroke and 85 μm L-stroke. Plots of T-stroke versus drive voltage and T-stroke versus apparent power (V*I) for these measurements appear in FIGS. 13 and 14, respectively.

Figure 13:
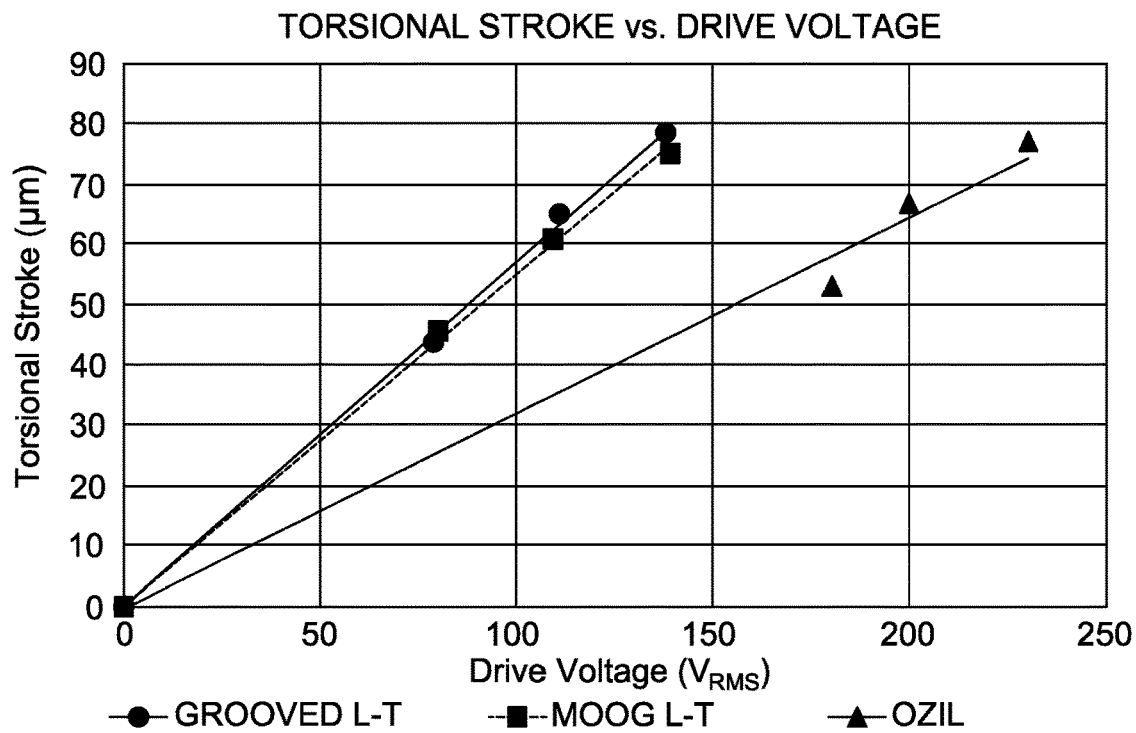
FIG. 13 is a plot of torsional stroke as a function of drive voltage showing measurement results of high power testing conducted for the Alcon OZil® handpiece assembly shown FIG. 2, the Moog L-T handpiece assembly shown in FIG. 3, and a Grooved L-T handpiece assembly of the present disclosure.

High power T mode performance characteristics are similar for the Moog L-T and the Grooved L-T handpiece assemblies. The drive voltage and minimum impedance are roughly equivalent, as are the power factor, T-stroke and T-stroke per volt. The T mode resonant frequency is roughly 2 kHz lower for the Grooved L-T assembly when compared to the Moog L-T assembly. To increase the T mode resonant frequency of the Grooved L-T assembly so that it matches the T mode resonant frequency of the Moog L-T assembly, the high gain section 42 of horn 12 would need to be shortened by 1.9 mm making the Grooved L-T handpiece 5.9 mm (0.23 inch) shorter than the Moog L-T handpiece, as shown in FIG. 15. By varying the depth of groove 50 located at a vibration node of the first L-T mode, the high power performance characteristics for the Moog L-T and Grooved L-T assemblies, as reflected in Table 2 and plotted in FIGS. 13 and 14, are comparable. This is achieved using groove depth to adjust the first L-T mode resonant frequency relative to the T mode resonant frequency rather than increasing the length of the horn unity gain (low gain) section and spacer for the Moog L-T handpiece assembly shown in FIG. 15. The axially shortened low gain section 40 of horn 12 and axially shortened spacer of the Grooved L-T assembly, combined with the axially shortened high gain section 42 of the horn, provision of groove 50, and use of six PZT8 ceramic rings as opposed to four PZT8 ceramic rings, produce a Grooved L-T handpiece assembly with similar high power performance to the Moog L-T handpiece assembly but which weighs 26.8 grams compared to 33.2 grams for the Moog L-T handpiece assembly. In addition, the Grooved L-T handpiece assembly is 0.23 inch shorter. The noticeably lighter (6.4 grams) and shorter Grooved L-T handpiece assembly helps to alleviate surgeon fatigue.

A comparison of L mode high power performance for the Grooved L-T handpiece assembly and the Moog L-T handpiece assembly indicates that the drive voltage and minimum impedance are higher for the Moog L-T assembly, and the power factor is lower for the Moog L-T assembly. L stroke is similar for both assemblies, and L-stroke per volt is lower for the Moog L-T assembly. In general, high power L mode performance at 5 W for the Grooved L-T assembly is improved relative to Moog L-T assembly.

Comparing T mode high power (5 W) stroke test results for the Grooved L-T assembly recorded in Table 2 and plotted in FIGS. 13 and 14 to T mode results for the OZil® assembly, drive voltage required by the OZil® assembly is more than double that needed by the Grooved L-T assembly to generate the same T stroke of 44 μm. The higher drive voltage and current required by the OZil® assembly result from a much lower T mode power factor of 0.24 for OZil® compared to 0.99 for the Grooved L-T assembly. The lower power factor of the OZil® assembly stems from a weaker T mode resonance and a higher minimum impedance. Based upon these results, as well as the low power performance results, T mode performance of the Grooved L-T assembly is a significant improvement over that of the OZil® assembly. A power factor of 0.6 for the OZil® assembly in L mode is less than the power factor of 0.9 for the Grooved L-T assembly in L mode. As a result, the OZil® assembly requires higher voltage and current than the Grooved L-T assembly to produce 5 W of real power with both handpiece assemblies generating roughly the same L-stroke. Based upon the results presented in Table 2, L mode performance of the Grooved L-T assembly is also an improvement over L mode performance of the OZil® assembly.

Handpiece assembly 10 of the present disclosure is designed for cataract surgery, but may be adapted for application in L-T handpieces used for other surgical procedures such as dental surgeries, orthopedic surgeries, bone surgeries, etc., as well as for non-surgical industrial applications such as drilling (e.g., hard rock drilling), coring, and material removal. Handpiece assembly 10 of the present disclosure may also find application in replacing a more complicated ultrasonic drill such as the one used by NASA in Mars exploration and described in U.S. Pat. Nos. 6,863,136; 6,968,910; and 7,156,189.

Although the present disclosure describes one or more particular embodiments, it will be understood that other embodiments of the present disclosure may be made without departing from the scope of the present disclosure. Hence, the present disclosure is deemed limited only by the appended claims and the reasonable interpretation thereof.

What is claimed is:

1. An ultrasonic handpiece assembly comprising:
   a horn elongated along a longitudinal axis, the horn including a rear end, a front end opposite the rear end, and a horn lumen extending axially through the horn;
   a rear mass attached to the rear end of the horn, the rear mass having a rear mass lumen extending axially through the rear mass and communicating with the horn lumen;

a plurality of piezoelectric elements arranged coaxially about the horn in a stack; and an L-T spring arranged coaxially about the horn axially behind the stack of piezoelectric elements;

wherein the horn includes a low gain section axially in front of the stack of piezoelectric elements and a high gain section axially in front of the low gain section, wherein the high gain section has a transverse cross-sectional area less than a transverse cross-sectional area of the low gain section;

wherein the low gain section of the horn includes a circumferential groove;

wherein the ultrasonic handpiece assembly has a first L-T mode at a first resonant frequency, a T mode at a second resonant frequency, a second L-T mode at a third resonant frequency, and an L mode at a fourth resonant frequency; and wherein the circumferential groove is arranged at an axial location corresponding to a vibrational node of the first L-T mode.

2. The ultrasonic handpiece assembly according to claim 1, further comprising a needle attached to the front end of the horn, the needle having a needle lumen extending axially through the needle and communicating with the horn lumen, wherein torsional vibration of the first L-T mode interacts constructively with torsional vibration of the T mode to increase a torsional stroke at a tip of the needle when the ultrasonic handpiece assembly is operated in the T mode.

3. The ultrasonic handpiece assembly according to claim 1, wherein the circumferential groove has a depth such that the second resonant frequency exceeds the first resonant frequency by a frequency differential in a range from 1.3 kHz through 2.2 kHz.

4. The ultrasonic handpiece assembly according to claim 1, further comprising a spacer arranged coaxially about the horn adjacent the rear mass.

5. The ultrasonic handpiece assembly according to claim 1, wherein the low gain section of the horn is a unity gain section.

6. The ultrasonic handpiece assembly according to claim 1, wherein the low gain section of the horn is cylindrical and has a diameter of 0.375 inches (9.52 mm) and the circumferential groove is 0.22 inches (5.588 mm) in axial length and has a radial depth in a range from 0.05 inches (1.270 mm) through 0.08 inches (2.032 mm).

7. The ultrasonic handpiece assembly according to claim 6, wherein the radial depth of the circumferential groove is 0.0555 inches (1.397 mm).

8. The ultrasonic handpiece assembly according to claim 1, wherein the low gain section of the horn is cylindrical and has a diameter of 0.5 inches (12.7 mm) and the circumferential groove is 0.22 inches (5.588 mm) in axial length and has a radial depth in a range from 0.04 inches (1.016 mm) through 0.08 inches (2.032 mm).

* * * * *